(12) United States Patent
Parker

(10) Patent No.: US 7,985,213 B2
(45) Date of Patent: Jul. 26, 2011

(54) DELIVERY CATHETER AND METHOD OF MANUFACTURE

(75) Inventor: Fred T. Parker, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1668 days.

(21) Appl. No.: 10/832,183

(22) Filed: Apr. 26, 2004

(65) Prior Publication Data

US 2004/0236346 A1 Nov. 25, 2004

Related U.S. Application Data

(60) Provisional application No. 60/465,368, filed on Apr. 25, 2003.

(51) Int. Cl.
*A61M 25/00* (2006.01)

(52) U.S. Cl. ........................................ 604/523; 604/526

(58) Field of Classification Search .......... 604/523–526, 604/528, 529
See application file for complete search history.

(56) References Cited

U.S. PATENT DOCUMENTS

| | | | |
|---|---|---|---|
| 4,634,432 A | 1/1987 | Kocak | |
| 4,657,772 A | 4/1987 | Kocak | |
| 4,705,511 A | 11/1987 | Kocak | |
| 5,380,304 A | 1/1995 | Parker | |
| 5,700,253 A * | 12/1997 | Parker | 604/526 |
| 5,769,830 A | 6/1998 | Parker | |
| 5,795,325 A * | 8/1998 | Valley et al. | 604/509 |
| 6,045,734 A | 4/2000 | Luther et al. | |
| 6,383,171 B1 * | 5/2002 | Gifford et al. | 604/508 |
| 2001/0044595 A1 * | 11/2001 | Reydel et al. | 604/98.02 |
| 2003/0023204 A1 * | 1/2003 | Vo et al. | 604/103.07 |

FOREIGN PATENT DOCUMENTS

| | | |
|---|---|---|
| WO | 9524158 | 9/1995 |
| WO | 0035527 | 6/2000 |
| WO | 0320353 | 3/2003 |

OTHER PUBLICATIONS

International Search Report on Corresponding PCT application Serial No. PCT/US2004/012837, 2004.

* cited by examiner

*Primary Examiner* — Nicholas D Lucchesi
*Assistant Examiner* — Nathan R Price
(74) *Attorney, Agent, or Firm* — Richard J. Godlewski

(57) ABSTRACT

A flexible, kink-resistant, delivery catheter or sheath (83) for percutaneously delivering implantable medical devices. The delivery catheter sheath includes a flat wire coil (95) with uniform spacing between the turns, which is compression fitted about and proximal the distal portion of an inner, lubricous material polytetrafluoroethylene tube (84). The delivery catheter or sheath further includes an outer tube (85) of a heat formable polyamide material, which is heat formed and compressed through the spaces between the turns of the wire coil to mechanically connect to the roughened outer surface of the inner tube. The distal portion (87) of the inner tube is expanded and everted or folded-back over itself and connected to the distal end of the outer tube to form a lumen having a larger diameter than the rest of the catheter.

16 Claims, 13 Drawing Sheets

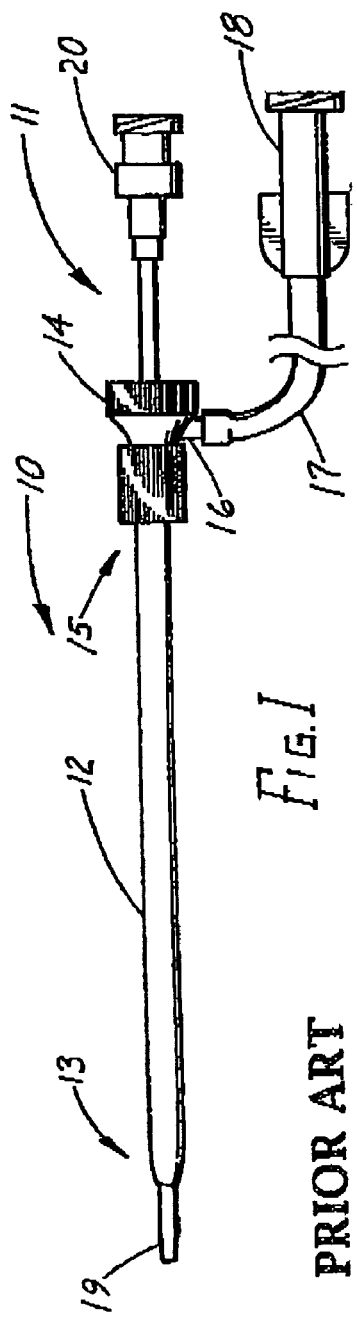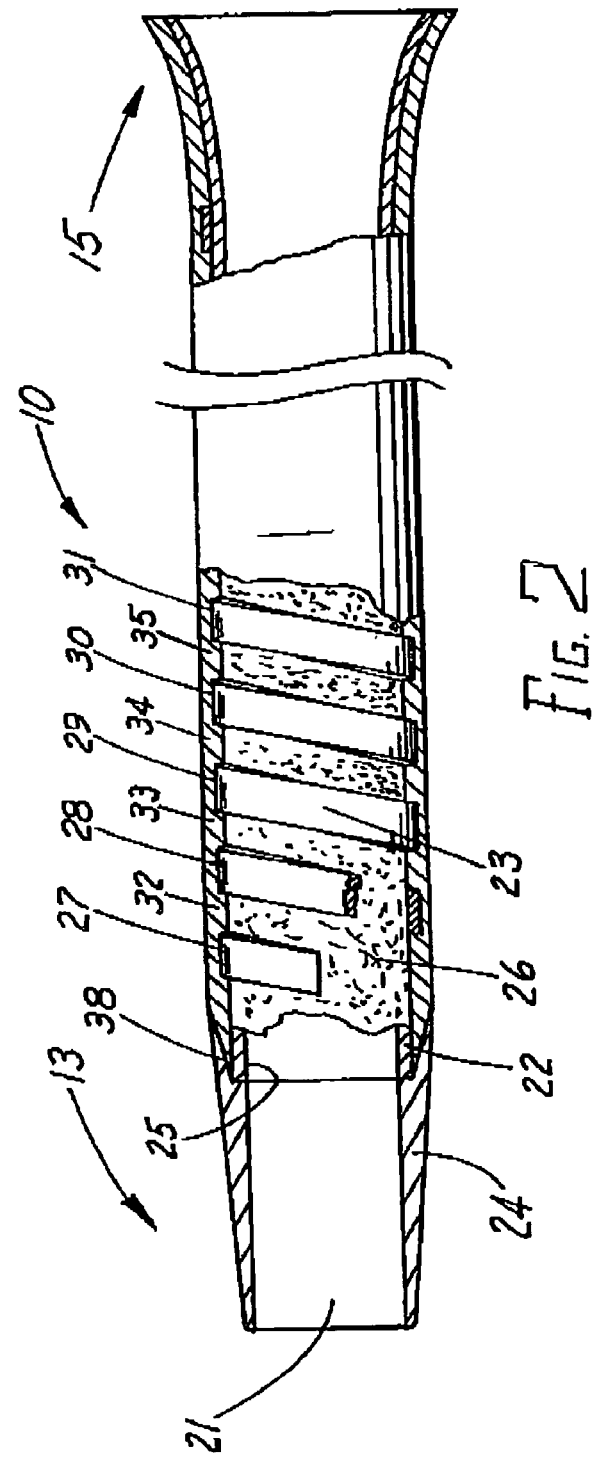
Fig. 1 PRIOR ART
Fig. 2 PRIOR ART

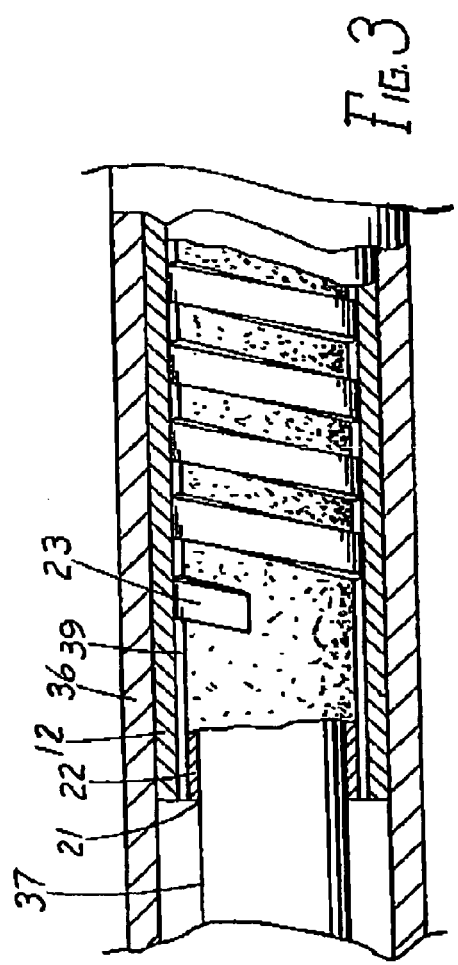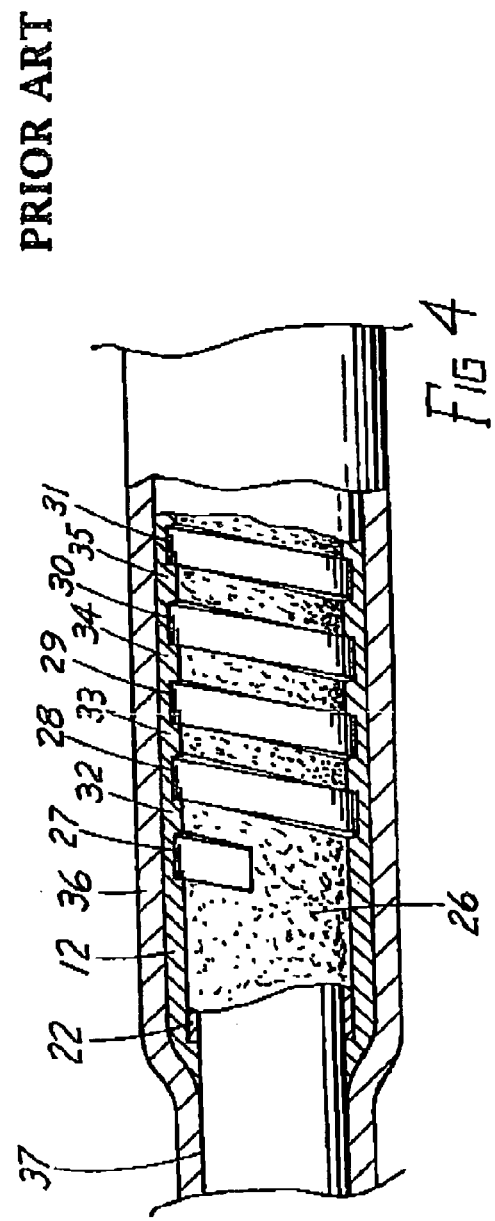

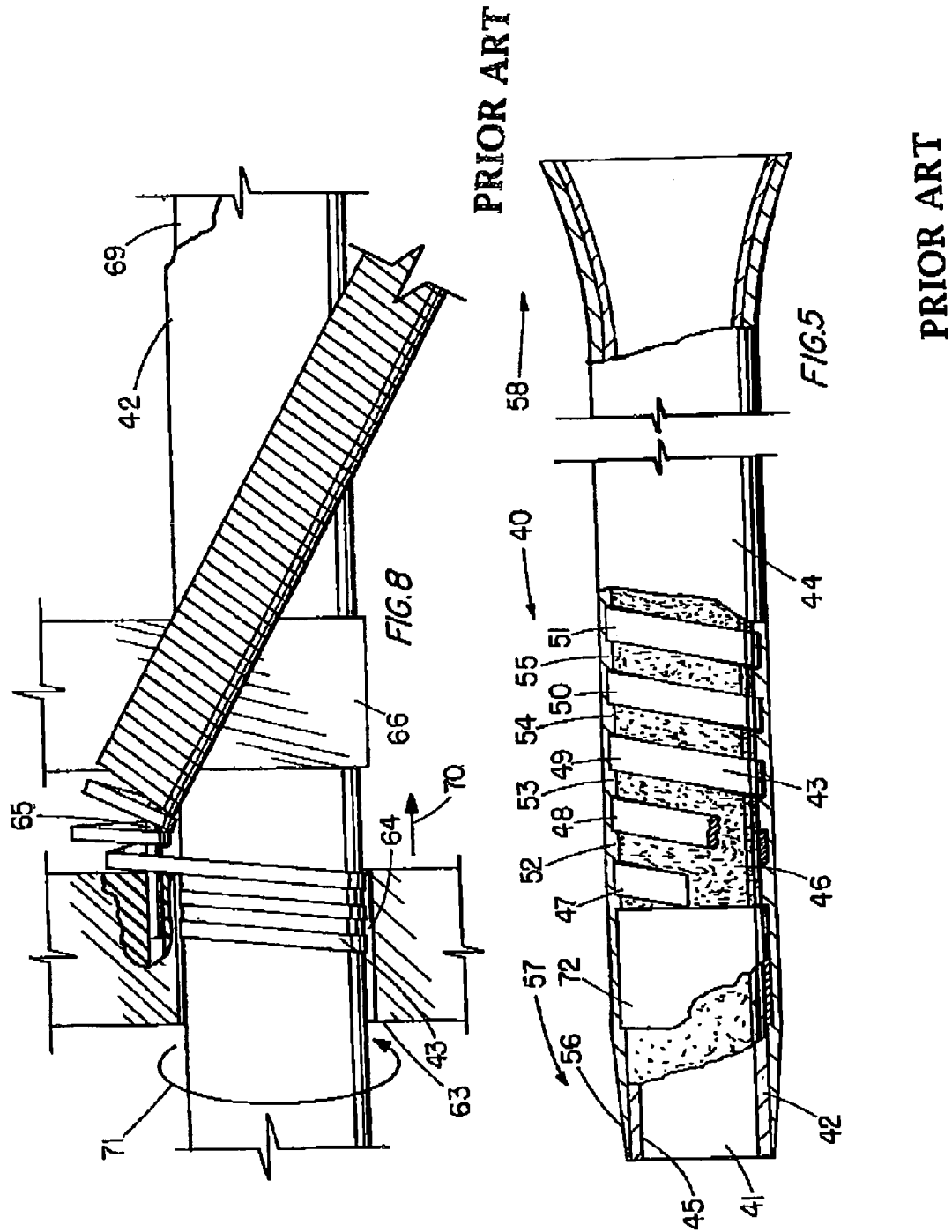

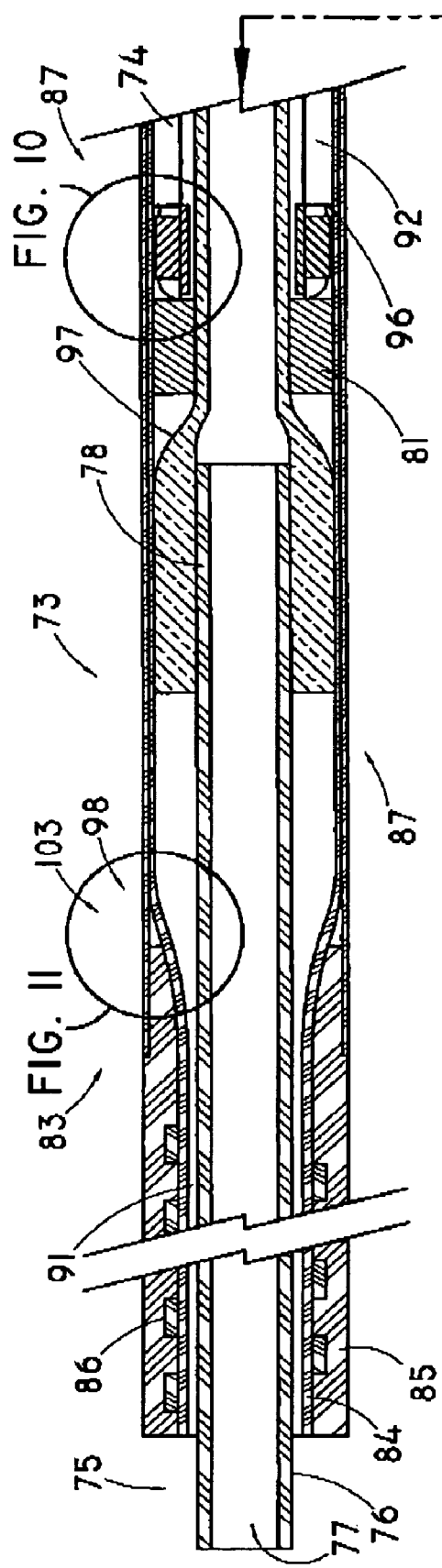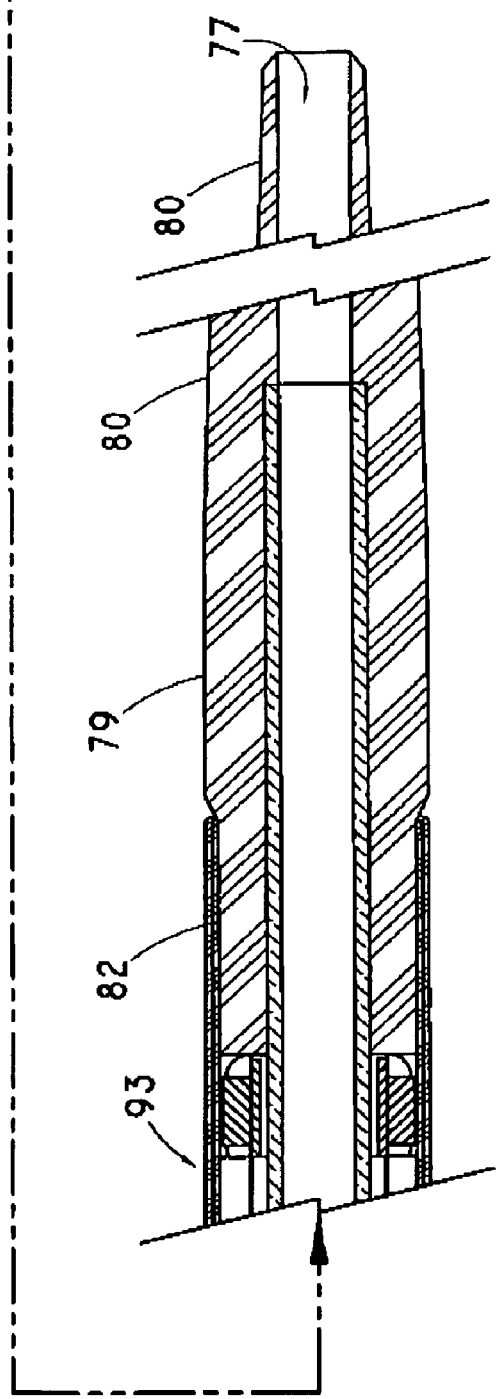

DELIVERY CATHETER AND METHOD OF MANUFACTURE

CROSS-REFERENCE TO RELATED APPLICATIONS

This application claims priority of provisional application Ser. No. 60/465,368, filed Apr. 25, 2003.

TECHNICAL FIELD

This invention relates generally to medical devices and, in particular, to delivery catheters/sheaths for delivering implantable medical devices to, for example, a vascular deployment site.

BACKGROUND OF THE INVENTION

Introducer sheaths are well-known for percutaneous vascular access and typically comprise polytetrafluoroethylene or fluorinated ethylene propylene. These sheaths are of a thin-wall construction, but tend to kink.
Increasing the thickness of the sheath wall minimally improves the level of kink resistance, which is still unacceptable. Sheaths used in hemofiltration and dialysis, in particular, are prone to kinking since they remain positioned in a patient's body for a long time. While positioned in a patient, the sheath may be bent or pinched off and, as a result, kink due to repeated use or patient movement. A kinked sheath is unusable and cannot be straightened while positioned in the body of a patient. Consequently, the sheath must be removed, leaving an enlarged, bleeding opening, which typically cannot be reused. Vascular access is then attempted at an alternative site, and the procedure is restarted. Restarting the procedure causes a time delay, which may be life threatening. In some cases, an alternative site is not available for introducing another sheath.

Another problem with thin-wall sheaths is that an emergency room physician will typically kink an introducer sheath while inserting various catheters therethrough during emergency procedures. Small diameter introducer sheaths are also typically bent and kinked under the time constraints of an emergency situation. As a result, a new sheath must be introduced at the same or another access site.

Another introducer sheath is described in U.S. Pat. Nos. 4,634,432; 4,657,772; and 4,705,511. This introducer sheath utilizes a helical coil spring and a cylindrical wall formed by dipping the spring in a protective coating composition, which completely surrounds the spring. The coating composition comprises a thermoplastic polymer material dissolved in a solvent solution. Although this introducer sheath appears to be more kink-resistant and flexible than a polytetrafluoroethylene sheath, the cylindrical wall is approximately twice as thick as that of the polytetrafluoroethylene sheath with the same inside diameter. The increased outside diameter of this introducer sheath significantly increases the size of the access site, which further accentuates the problem of bleeding.

Introducer sheaths relevant to this delivery catheter are described in U.S. Pat. Nos. 5,380,304 and 5,700,253. These introducer sheaths are flexible and kink-resistant and include typically a flat wire coil having a plurality of uniformly spaced turns positioned and compression fitted around an inner tube. An outer tube is connected to the inner tube through the uniform spacing of the coil turns. As a result, the compression fitted coil reinforces the wall to provide an extremely kink-resistant and thin-walled introducer sheath. Although extremely well suited for its intended purpose of gaining access to, for example, the vascular system, these introducer sheaths are typically of a relatively short length commonly in the neighborhood of eight centimeters, which is ideally suited for gaining vascular access. However, these and other relatively large introducers create large puncture sites, which are more difficult to control bleeding thereat, and do not track as well due to the added stiffness along its entire length.

In order to produce a smaller diameter introducer or catheter, the implantable, self-expanding stents have to be cut from a smaller cannula tube, which resulted in less radial force. Less radial force is thought to be not advantageous, since it is generally believed the higher the radial force of the stent, the better the final treatment will be. Stents cut or formed from smaller tubes or cannula often require the delivery system to have a smaller guide wire lumen, since the stent was being compressed to a smaller diameter. This is thought not to be desirable, since it does not give the support for implantable device positioning like a larger guide wire.

The ZILVER™ stent system of COOK Incorporated, Bloomington, Ind., utilizes a 7 French delivery system which includes a self-expanding stent that has a relatively high radial force compared to other stents in the market place. This stent system utilizes the FLEXOR™ sheath technology disclosed in U.S. Pat. Nos. 5,380,304 and 5,700,253. However, the introducer sheath technology described in these patents has been lengthened to function as a delivery catheter or sheath, which delivers stents over a standard 0.035 inch guide wire. Since this FLEXOR delivery catheter maintains essentially the same wall thickness throughout its length, the distal portion of the delivery catheter maintaining the stent in a compressed state is the limiting factor on reducing the French size (diameter) of the delivery system.

SUMMARY OF THE INVENTION

The foregoing problems are solved and a technical advance is achieved in an illustrative delivery catheter/sheath, which has an enlarged lumen or passageway at the distal end portion of the catheter than that of the remaining proximal portion of the delivery catheter/sheath. As a result, the outer diameter of the delivery catheter is advantageously reduced to reduce bleeding at the access site and to navigate smaller diameter and tortuous vessels. By way of example, the same self-expanding ZILVER stent as used in the commercially available 7 French delivery system can now be positioned in and delivered with a reduced diameter 6 French delivery system. This illustrative delivery catheter/sheath comprises a first or inner tube having a lumen or passageway extending longitudinally therein. A second or outer tube is positioned around and proximal a distal portion of the first or inner tube. The distal portion of the first or inner tube includes first and second coaxial layers, which are formed when the inner tube is everted or folded-back and connected to the outer tube. The wall of the inner tube is typically thinner than that of the outer tube. The distal portion of the inner tube is typically expanded so that the lumen or passageway therethrough has a larger cross-sectional area or diameter to accept the self-expanding ZILVER stent. As previously suggested, the FLEXOR sheath/technology typically includes a reinforcement, of, for example, a flat wire compression fitted coil positioned at least partially along and proximal the distal portion of the inner tube. The second or outer tube is positioned around the reinforcement and heat shrunk through the spacing between the turns of the coil. By everting or folding back the distal portion of the first or inner tube and then connecting it to the outer tube, the inner lumen or passageway of the distal portion is advantageously increased or maintained at a size much greater than that of the remaining proximal portion of the catheter, which includes the outer tube and the reinforcement.

In an alternative embodiment of the delivery catheter/sheath of the present invention, the distal portion of the first or inner tube comprises simply first and second coaxially layers of the first tube. As previously suggested, the distal portion of the inner tube has an increased or enlarged diameter.

To advantageously maintain structural integrity of the distal portion of the first or inner tube, an adhesive is disposed between the first and second layers or the everted/folded-back portion of the inner tube. This adhesive comprises a medical grade adhesive, preferably, an ultra-violet light cured glue or hot melt glue.

To complement the illustrative delivery catheter of the present invention, the delivery catheter further includes a pusher or central carrier disposed in the passageway or lumen of the inner tube. The pusher or central carrier has an annular recess in a distal portion thereof for compressing or disposing an implantable medical device such as a self-expanding stent therein. The distal portion of the delivery catheter is advanced over the annular recess in the distal portion of the pusher to maintain the stent in a small diameter or compressed state. To aid in radiographic visualization of the contained device and pusher, the pusher has a radiopaque marker disposed about a proximal end of the annular recess. The pusher also has a shoulder at a proximal end of the annular recess for engaging the wall of the inner tube as well as the proximal end of the radiopaque marker and/or the contained implantable medical device. Typically, the proximal end of the everted or folded-back portion of the delivery catheter extends proximal the annular recess of the pusher so as to advantageously maximize the diameter of the contained implantable medical device.

In another alternative illustrative embodiment of the present invention, the distal portion of the inner tube or the everted distal portion thereof, can include a reinforcement between the first and second layers of the first or inner tube. This reinforcement can advantageously include simply a coil of filament suture or round/flat wire between the first and second layers of the distal portion of the everted inner tube. This reinforcement advantageously contains the implantable medical device in its compressed state without gradual expansion into the inner tube material during extended periods of time while the delivery system is awaiting use.

The wall of the inner tube advantageously prevents the coil turns from extending into the inner tube passageway. As a result, the inner tube passageway has a uniform diameter for passing the largest possible diameter catheter therethrough. In contrast, the protrusion of coil turns into the passageway establishes a varying diameter, which limits the size of the catheter passable therethrough. The inner tube also comprises a lubricous material such as polytetrafluoroethylene, which presents a slippery surface for easy insertion of a catheter therethrough. Furthermore, the inner tube includes a smooth inner surface for resisting the formation of blood clots thereon. The inner tube also advantageously includes a rough outer surface for improving the connection of the outer tube thereto through the uniform spacing of the coil turns.

The outer tube advantageously comprises a heat formable polyamide material such as nylon for mechanically connecting with the rough outer surface of the inner tube. The sheath further comprises a heat shrinkable tube positioned around the outer tube for compressing the outer tube between the uniform spacing of the compression-fitted coil turns and mechanically connecting the outer tube to the rough surface of the inner tube when heated. The heat formable polyamide material is also advantageously self-leveling for providing a smooth outer surface which also reduces the formation of blood clots thereon.

The distal ends of the inner and outer tubes extend beyond the distal end of the coil. The distal end of the outer tube is tapered and extends beyond the distal end of the inner tube to advantageously prevent the inner tube from presenting a rough edge or surface, which may cause injury to the vessel wall. The inner diameter of the passageway about the distal ends of the inner and outer tubes is uniform to again minimize the formation of blood clots on the inner surface of the inner tube.

The proximal ends of the inner and outer tubes also extend beyond the proximal end of the coil and are flared for attachment to a connector.

In another aspect of the present invention, a coil having an inner diameter smaller than the outer diameter of the inner tube is wound and compression fitted around the inner tube. This advantageously eliminates collapsing the inner tube for insertion into the passage of the flat wire coil. This also advantageously eliminates the formation of any wrinkles in the inner tube when the collapsed inner tube is expanded to form a compression fit against the flat wire coil.

A radiopaque marker is positioned adjacent the distal end of the coil to improve visualization of the sheath when inserted in a patient.

The method of manufacturing a flexible, kink-resistant, introducer sheath includes expanding the flat wire coil with a inner diameter less than the outer diameter of the inner tube and wrapping the coil when expanded around the inner tube. The outer tube is then longitudinally positioned around the inner tube and flat wire coil and connected to the inner tube through spaces between the turns of the coil.

BRIEF DESCRIPTION OF THE DRAWING

FIG. 1 depicts an illustrative flexible, kink-resistant, introducer sheath of the present invention;

FIG. 2 depicts a partially sectioned view of the introducer sheath of FIG. 1;

FIG. 3 depicts a partially sectioned view of the introducer sheath of the present invention with a heat shrink tube prior to being heated;

FIG. 4 depicts a partially sectioned view of the introducer sheath of FIG. 3 with the heat shrink tube heated and the outer tube resultingly formed;

FIG. 5 depicts a partially sectioned view of another aspect of the present invention and an alternative embodiment of the sheath of FIG. 2;

FIG. 8 depicts an enlarged view of a portion of the coil transfer mechanism of FIG. 7;

FIG. 9 depicts a longitudinal section side view of a delivery catheter of the present invention;

DETAILED DESCRIPTION

Figure 7:
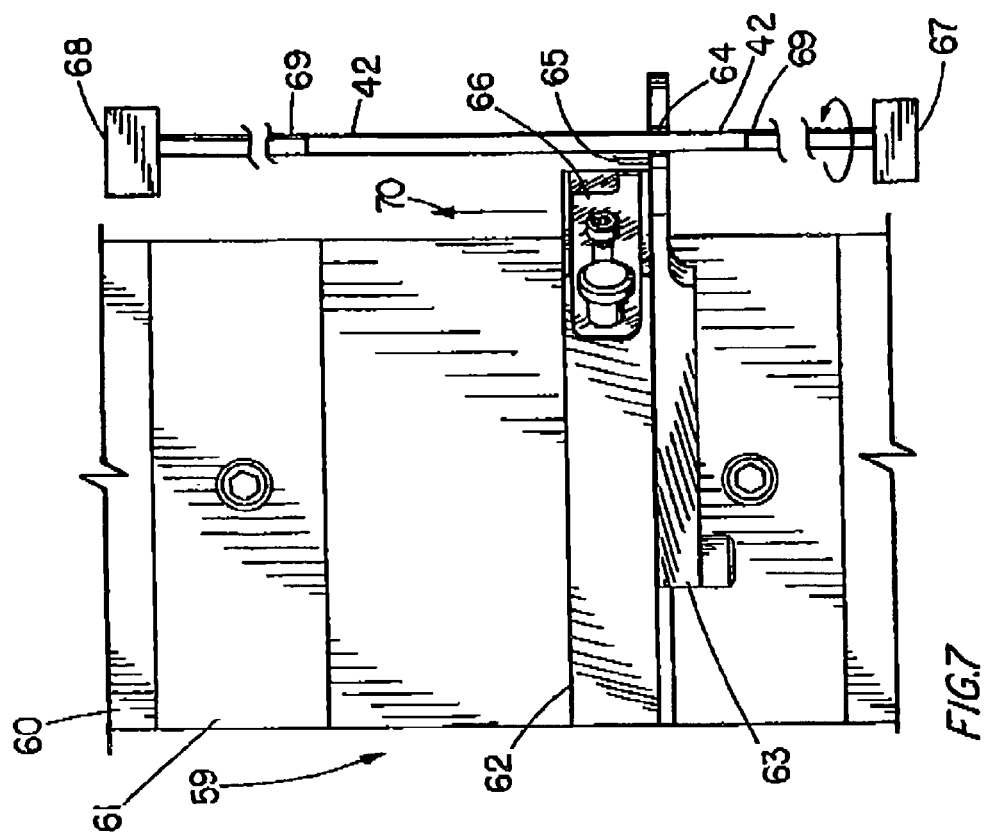
FIG. 7 depicts a top view of the coil transfer mechanism of FIG. 6.

FIG. 1 depicts an illustrative flexible, kink-resistant, introducer sheath 10 with a tapered dilator 11 extending longitudinally through the passageway of the sheath. As shown, the introducer sheath includes an outer tube 12 with a tapered distal end 13 and connector valve 14 attached about proximal end 15 of the sheath. Well-known connector valve 14 includes a silicone disk (not shown) for preventing the backflow of fluids therethrough. The disk includes a slit for the insertion of dilator 11. Byway of example, the dilator 11 has a 6.0 French (0.079") outside diameter. Connector 14 also includes side arm 16 to which polyvinyl tube 17 and male Luer lock connector 18 are connected for introducing and aspirating fluids therethrough. Dilator 11 includes tapered distal end 19 for accessing and dilating a vascular access site over a well-known and commercially available wire guide. The guide is inserted in the vessel with an introducer needle using, for example, the well-known percutaneous vascular access Seldinger technique. A well-known male Luer lock connector hub 20 is attached at the proximal end of the dilator for connection to syringes and other medical apparatus.

Depicted in FIG. 2 is a partially sectioned view of introducer sheath 10 with dilator 11 removed from longitudinal passageway 21. The sheath comprises inner tube 22, flat wire coil 23 compression fitted therearound, and outer tube 12 mechanically connected to roughened outer surface 26 of the inner tube through the spacings of the coil. Inner tube 22 is a 7.4 cm length of a lubricous material tube such as polytetrafluoroethylene having a uniform inside diameter in the range of 0.0825" to 0.0840" with a wall thickness of 0.0015" plus or minus 0.0005" before heating. The inner tube has a minimum inside dimension of 0.081" after heating. The lubricous polytetrafluoroethylene material presents a slippery inner surface 25 for the easy insertion and withdrawal of the dilator as well as other catheters and medical apparatus. Inner surface 25 is also smooth and nonporous for minimizing the formation of blood clots and other thrombi thereon. Outer surface 26 of the inner tube is chemically etched in a well-known manner for forming a rough outer surface to which outer tube 12 is mechanically connected using a well-known heat shrinking and formation process. The uniform inner diameter of inner tube 22 extends the entire length of passageway 21 for passing the largest possible diameter catheter therethrough. The wall of the inner tube prevents the turns of compression-fitted coil 23 from protruding into inner tube passageway 21.

Coil 23 comprises a plurality of flat wire turns, for example, 27-31, with uniform spacing including equal width spaces 32-35 therebetween. Coil 23 is 6.5 cm in length with an outside diameter of 0.0942" plus or minus 0.020" formed from 0.03" thick by 0.12" wide flat rectangular stainless steel wire wound with a uniform space in the range of 0.05" to 0.15" between the turns of the coil. Wire coil 23 is compression fitted around the outer surface of inner tube 22 approximately 4 mm from the distal end thereof and approximately 5 mm from the proximal end thereof to maintain the uniform spacing between the turns of the coil. The coil is compression fitted by collapsing inner tube 22 and inserting the wire coil thereover. Inner tube 22 is then compressed-air expanded to engage and compression fit the inner surface of the flat wire coil. A mandril inserted through the passageway of the inner tube further compresses the inner tube against the coil turns during the manufacture of the sheath as hereinafter described. The coil is positioned away from the distal and proximal ends of the inner tube to permit tapering and flaring of the sheath without extending the coil turns through the polyamide material of the outer tube.

Outer tube 12 is 7.4 cm in length with an inside diameter of 0.103" plus or minus 0.02" of a heat formable polyamide material such as nylon that is heat shrunk through the turn spacings of coil 23, which in turn is compression fitted over inner tube 22. The wall thickness of the nylon tube is approximately 0.065" plus or minus 0.01". The outer tube is heated and compressed through the spaces between the coil turns with a heat shrink tube for mechanically connecting to rough outer surface 26 of the inner tube. As a result, the outside diameter of the outer tube is approximately 0.22" greater than that of the inner tube. After the outer tube is heat shrunk onto the roughened surface of the inner tube, the shrink tube is removed therefrom, and a taper formed at the distal end of the sheath. As a result, the thickness of the sheath including the inner tube, coil, and outer tube is approximately 0.11". The 4 mm length about the distal end of the inner and outer tubes are cut to within a range of 0.10" to 0.90" from the end of coil 23 depending on the inside diameter of the sheath. For a 6.0 French introducer sheath, approximately 0.20" of outer tube 12 is externally tapered about the distal end in a well-known manner to form contact surface area 38. Tapered distal end 13 is formed by cutting and slitting a 3 mm length of nylon tubing having a 0.100" inside diameter and inserting it into a well-known taper mold. The short length of tubing is heated, and the distal end of the sheath with a mandril inserted therethrough is inserted into the taper mold to thermally bond nylon tip material 24 to the outer tube and to form tapered distal end 13, as shown. As a result, the inside diameter of outer tube 12 and inner tube 22 about the distal end thereof assumes the uniform inner diameter of the inner tube. After the distal end is tapered, the outer tube extends approximately 0.120" beyond the distal end of the inner tube and 0.140" beyond the distal end of the flat wire coil. The distal end of inner tube 22 may vary along the length of the tapered distal end of the outer tube, but should not extend all the way to the distal end of the outer tube so as not to break the tapered surface of the outer tube. In this particular embodiment, nylon tip material 24 is of the same durometer as that of outer tube 12. However, it is contemplated that the tip material may have a durometer other than that of the outer tube material. It is further contemplated that the tip material may have a harder durometer so as to further facilitate entry into the access site. Proximal end 15 of the sheath is formed into a flared configuration in a well-known manner such as inserting over a heated, tapered tip end and then cooled.

FIG. 3 depicts a partially sectioned view of introducer sheath 10 with heat shrink tube 36 positioned over outer tube 12 and flat wire coil 23 with longitudinal space 39 therebetween. As previously described, flat wire coil 23 is compression fitted around inner tube 22. Prior to heating shrink tube 36 and forming outer tube 12, mandril 37 is inserted through passageway 21 to further maintain the uniform spacing between the coil turns. As shown, heat shrink tube 36 is somewhat longer than nylon outer tube 12 and has an inside diameter in the range of 0.825" to 0.840" with a wall thickness of approximately 0.015" plus or minus 0.005". The heat shrink tube is preferably of a fluorinated ethylene propylene heat formable material. The nylon outer tube has a processing temperature range for the heat formation thereof in the range of 356 to 500 degrees Fahrenheit.

FIG. 4 depicts heat shrink tube 36 being oven heated to a temperature of 365 degrees Fahrenheit, which is in the processing temperature range of the nylon outer tube material. As the heat shrink tube shrinks, the heated nylon outer tube material 12 is compressed between coil turns 27-31 in uniform spaces 32-35 to mechanically connect with roughened surface 26 of inner tube 22. The heat formable nylon material tube is also self-leveling, which provides a uniform outer diameter surface for the sheath. Heat shrink tube 36 is then split from the sheath. As previously described, distal end 13 is tapered, and proximal end 15 is flared.

Depicted in FIG. 5 is a partially sectioned view of introducer sheath 40, which represents another aspect of the present invention and an alternative embodiment of introducer sheath 10 of FIG. 2. Introducer sheath 40 includes coaxial inner tube 42, flat wire coil 43, and outer tube 44 with tapered distal end 57 and flared proximal end 58. As previously described, a connector valve 14 is inserted into flared proximal end 58 of the sheath for preventing the backflow of fluids therethrough. The sheath is formed by first winding and compression fitting flat wire coil 43 around inner tube 42 and then heat shrinking and mechanically connecting outer tube 44 to roughened outer surface 46 of the inner tube through the spaces between the coil turns. Radiopaque marker sleeve 72 is positioned distally of the flat wire coil between the inner and outer tubes near the distal end of the sheath. Unlike flat wire coil 23 of sheath 10 in FIG. 2, flat wire coil 43 of FIG. 5 is wound around inner tube 42 to form the compression fit between the inner tube and wire coil. The coil is wound around the inner tube by expanding and wrapping the coil around the inner tube using, for example, a commercially available lathe and a transfer mechanism attached to the carriage of the lathe, which will be described hereinafter. This winding technique improves the manufacturing process and maintains closer tolerances for the uniform spacing between the turns of the coil. In addition, the inner tube is not compressed or collapsed for insertion into the passage of the flat wire coil. This advantageously eliminates any wrinkles in the inner tube wall and maintains closer manufacturing tolerances.

By way of example, kink-resistant, introducer sheath 40 is a 9.6 French (0.126") sheath for inserting a 9.6 French dilator therethrough. Inner tube 42 is a 31 cm length tube of a lubricious material such as polytetrafluoroethylene having a uniform inside diameter in the range of 0.1267" to 0.1282" with a wall thickness of 0.02"±0.013". The inner tube has a minimum inside diameter of 0.126". The lubricious polytetrafluoroethylene material presents a slippery inner surface 45 for easily inserting and withdrawing a dilator as well as other catheters and medical apparatus therethrough. Inner surface 45 is also smooth and nonporous for minimizing the formation of blood clots and other thrombi thereon. Outer surface 46 of the inner tube is chemically etched in a well-known manner for forming a rough outer surface to which outer tube 44 is mechanically connected using the previously described heat shrinking process.

Coil 43 comprises a plurality of flat wire turns, for example, 47-51 with uniform spacing including equal width spaces 52-55 therebetween. Coil 43 is 30 cm in length with an outside diameter of 0.80"±0.05" prior to annealing. The coil is annealed by baking the coil at 800° F.±25° for approximately ten minutes. After annealing, the outside of the coil has a nominal dimension of 0.85". The coil is formed from 0.04" thick by 0.12" wide flat rectangular stainless steel wire wound with a uniform space in the range of 0.05" to 0.10" between the turns of the coil. Prior to being wound around inner tube 42, wire coil 43 has an inside diameter which is at least 0.40" smaller than the outside diameter of the inner tube. Wire coil 43 is wound and compression fitted around outer surface 46 of inner tube 42 approximately 3-4 mm from the distal end thereof and approximately 5 mm from the proximal end thereof to taper and flare the distal and proximal ends, respectively. After being wound around the outer surface of the inner tube, the spacing between the turns of the coil is approximately 0.07" to 0.09". The coil is wound and compression fitted around inner tube 42 by inserting a mandril having, for example, an outside diameter of 0.1260"+0.002"-0.000" through passage 41 of the inner tube and positioning the mandril and tube into the head and tail stock of a commercially available lathe such as the Grizzly Model No. G-1550. A transfer mechanism, as depicted in FIGS. 6-8, is mounted on the carriage of the lathe to wind and compression fit the coil around the inner tube.

Outer tube 44 is 31 cm in length with a preshrunk inside diameter of 0.145"±0.02" and consists of a heat formable polyamide material such as radiopaque nylon that is heat shrunk through coil 43. The outer tube has a nominal preshrunk outside diameter of 0.158". The wall thickness of the nylon tube is approximately 0.065"±0.01". After the outer tube is heat shrunk and mechanically connected to the inner tube through the turns of the flat wire coil, sheath 40 has a overall nominal wall thickness of 0.11" with an outside diameter of 0.149"±0.02". Tapered distal end 57 of the sheath is formed by grinding externally tapered surface 56 on the distal end of outer tube 44 for a distance of approximately 2 mm from the distal end of radiopaque marker 72. The flared proximal end extends for approximately 5 mm from the proximal end of flat wire coil 43 and is formed using a well-known flaring tool with heat applied to the proximal ends of the tubes.

Prior to heat shrinking the outer tube to the inner tube, radiopaque marker 72 is inserted over the distal end of the inner tube next to flat wire coil 43. Radiopaque marker 72 is approximately 0.50"±0.05" long with an outside diameter of 0.139"±0.005" and an inside diameter of 0.134"±0.005". The marker comprises, for example, 10 percent iridium with the remainder being a platinum material.

Figure 6:
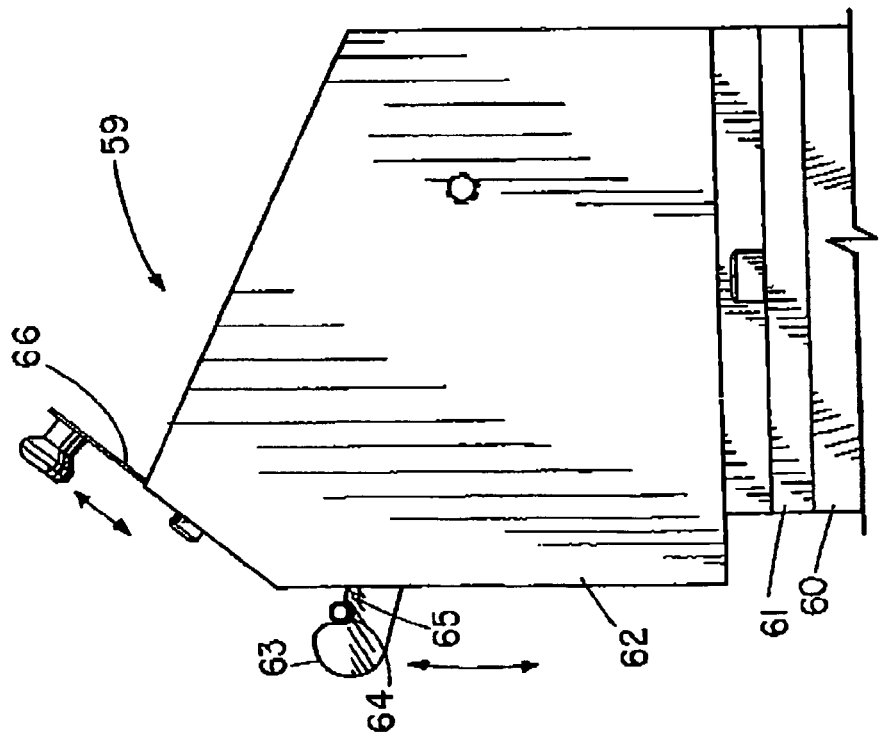
FIG. 6 depicts a side view of a coil transfer mechanism for winding and compression fitting a coil around an inner tube of the sheath of FIG. 5.
Figure 10:
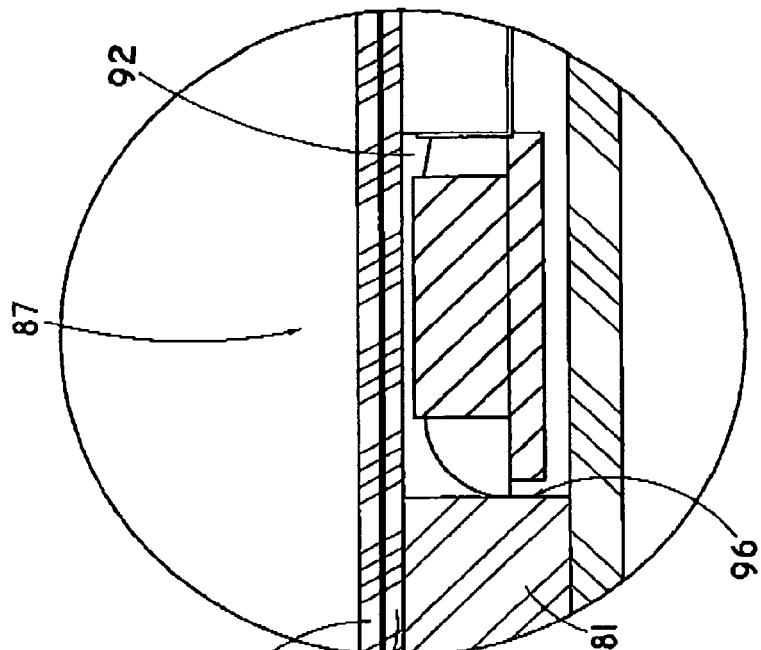
FIG. 10 depicts an enlarged cross sectional side view of a portion of the delivery catheter and contained stent of FIG. 9.

Depicted in FIG. 6 is a side view of coil transfer mechanism 59 mounted on carriage 60 of a commercially available lathe such as the previously identified Grizzly Model No. G-1550. This side view is viewed from the tail stock end of the lathe. The coil transfer mechanism includes adapter plate 61, which is horizontally mounted on the carriage of the lathe, and tool holder 62, which is vertically mounted on the horizontal adapter plate. Pivotedly mounted on the tool holder is adjustable guide support 63 with semicircular recess 64 extending through the guide support adjacent the free end thereof. Extending perpendicularly from the guide support toward the tail stock of the lathe is coil retaining pin 65. The coil retaining pin engages the flat wire coil to unwrap the coil while the lathe rotates a mandril with the inner tube mounted thereon. While the mandril and inner tube are being rotated the expanded coil is being wrapped and compression fitted on the outer surface of the inner tube. The transfer mechanism also includes adjustable shield 66 which is positioned adjacent the rotating inner tube to prevent the flat wire coil, which is being unwrapped, from scoring the surface of the inner tube.

Depicted in FIG. 7 is a top view of coil transfer mechanism 59 mounted on lathe carriage 60. Also depicted is head stock 67 and tail stock 68 of the lathe with mandril 69 and inner tube 42 rotatably mounted therebetween. Adjustable guide support 63 has been positioned to cradle mandril 69 and inner tube 42 in recess 64 of the support. Coil retaining pin 65 faces toward tail stock 68 and is adjacent to the rotating mandril and inner tube. The longitudinal axis of the retaining pin and mandril are substantially parallel to one another. Adjustable shield 66 is depicted in a raised position in order to mount the mandril and inner tube between the tail and head stocks. As flat wire coil 43 is wound around inner tube 42, the coil transfer mechanism and the carriage of the lathe move relative to the head and tail stocks as indicated by arrow 70.

FIG. 8 depicts an enlarged view of adjustable guide support 63 and adjustable shield 66 of FIG. 7 with inner tube 42 and mandril 69 positioned therebetween in recess 64 of the support. To start the coil winding process, several turns of coil 43 are manually wrapped around the distal end of inner tube 42 mounted on mandril 69. The next several turns of the wire coil are positioned over coil retaining pin 65, as depicted. Adjustable shield 66 is then slid down and adjacent the inner tube to prevent the remaining free end of the coil from scoring the surface of the rotating inner tube. The lathe is turned on and rotated in the direction of arrow 71 to expand the coil with retaining pin 65 and wrap the coil turns around the outer surface of the rotating inner tube. The coil transfer mechanism moves as indicated by arrow 70 at a speed controlled by the lathe carriage to control the spacing between the coil turns. A uniform spacing between the coil turns of 0.07" to 0.09" is easily maintained using this coil winding procedure. After the desired length of coil is wrapped around the inner tube, the mandril, inner tube and wrapped wire coil are removed from the lathe. The outer radiopaque marker 72 is positioned adjacent the distal end of the coil, and outer tube 55 with a shrink wrap tube positioned thereover is coaxially positioned over the wrapped wire coil and inner tube. The outer tube is then heat shrunk and mechanically connected to the inner tube through the turns of the flat wire coil as previously described with respect to the procedure detailed in FIGS. 3 and 4.

FIG. 9 depicts a longitudinally sectioned side view of delivery catheter 83 of the present invention as part of delivery system 73 with pusher or central carrier 75 disposed in passageway or lumen 91 of the delivery catheter. The pusher includes an annular recess 92 in distal portion 93 of the pusher. Contained within the annular recess of the pusher is an implantable medical device 74 such as a self-expanding ZILVER stent in a compressed or reduced diameter state. The distal end portion 87 of the delivery catheter 83 extends over the compressed state stent 74 and annular recess 92 of the pusher. Thus, the distal portion 87 of the delivery catheter maintains the self expanding stent 74 in a compressed state until the delivery system, delivery catheter and stent is positioned at, for example, a vascular deployment site. The delivery catheter is then pulled back in a proximal direction with respect to the pusher thus uncovering and releasing the compressed state self-expanding stent.

Delivery catheter 83 comprises a first or inner tube 84 of, for example, a lubricous material, preferably, polytetrafluoroethylene (PTFE) having a passageway or lumen 91 extending longitudinally therethrough or therein. A reinforcement 86 such as preferably a stainless flat wire coil with uniformly spaced turns is preferably compression fitted as previously described and positioned at least partially along and proximal distal portion 87 of the inner tube. A second or outer tube 85 of, for example, a polyamide, preferably, PEBAX, an ether block polyamide, is positioned around the reinforcement and the inner tube proximal distal portion 87 of the inner tube. The outer tube is connected to the roughened outer surface of the inner tube through the reinforcement such as the uniform spacing between the turns of the flat wire coil. As previously described, a heat shrink tube is positioned around the outer tube and then heated to compress the outer tube material through the turns of the coil and connect it to the roughened outer surface of the inner tube. The distal portion 87 of the inner tube is expanded over a mandril and then everted or folded-back over itself and then connected to the distal end 103 of the outer tube 85.

Figure 11:
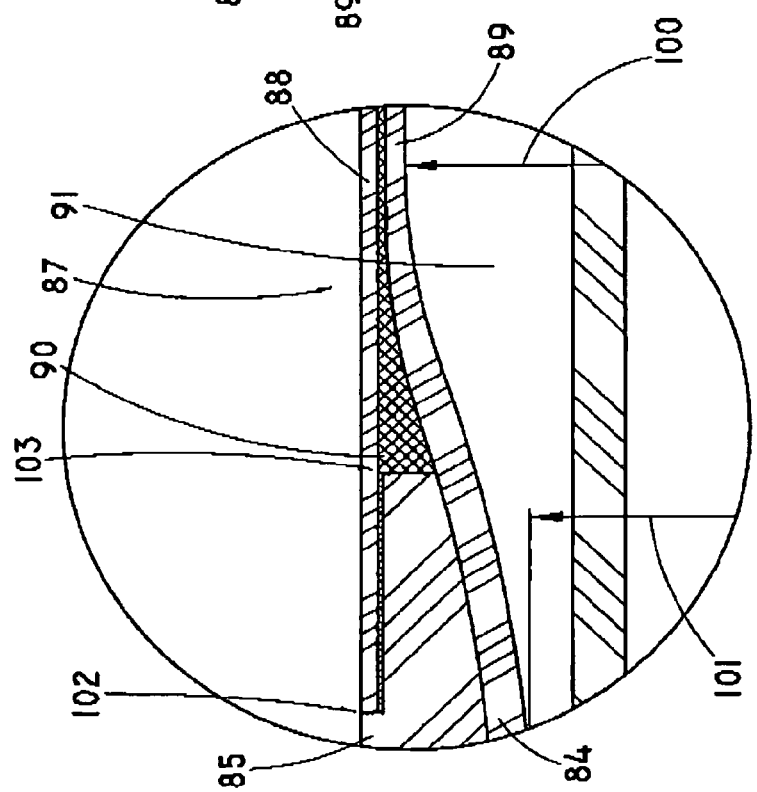
FIG. 11 depicts an enlarged cross sectional view of the inner tube and connection to the outer tube of the delivery catheter of FIG. 9.

FIG. 11 depicts an enlarged cross sectional view of the proximal end 98 of the distal portion 87 of the inner tube connected to the distal end 103 of outer tube 85. As depicted, passageway or lumen 91 through distal portion 87 of the delivery catheter has a larger cross-sectional area or diameter 100 than the cross-sectional area or diameter 101 proximal distal portion 87. As a result, larger diameter stents can be compressed and positioned in annular recess 92 of the pusher and contained in distal portion 87 of the delivery catheter. Accordingly, a self-expanding ZILVER® stent previously implanted with a 7 French delivery system can now be delivered with this reduced diameter 6 French delivery catheter and system.

First or inner tube 84 with smaller diameter 101 is drawn or pulled over a mandril having an outer diameter 101 thus stretching the distal portion of the inner tube material and expanding passageway or lumen 91 to larger diameter 100. With the distal portion of the inner tube expanded over the large diameter mandril a coating of an adhesive 90 is applied to the outer surface of the inner tube. The distal end 102 of the inner tube is then grasped and everted or folded back over itself with the adhesive acting as a lubricant during the fold back or eversion step. The distal end 102 of the inner tube is folded back and connected to the distal end 103 of outer tube 85 also with the aid of adhesive 90. Adhesive 90 is a medical grade adhesive and preferably an ultra-violet light cured glue such as No. 3311 from Loctite Corporation, Fort Wayne, Ind., or a commercially available hot melt glue such as Loctite No. 3640-42 polyamide hot melt glue. After the UV glue is exposed to ultra-violet light, the glue acting previously as a lubricant adheres first or outer layer 88 of the inner tube to the second or inner layer 89 layer of the inner tube, thus forming the everted or folded-back distal portion 87 of the inner tube. Adhering distal end 102 of the outer layer of the inner tube to the outer tube further provides an integral delivery catheter that will not come apart during a medical procedure.

FIG. 9 also depicts second or outer tube 85 positioned around and proximal distal portion 87 of the first or inner tube 84. Reinforcement 86 such as preferably a flat wire coil as previously described is positioned at least partially along and proximal distal portion 87 of the inner tube. Outer tube 85 is positioned around the reinforcement and connected through the inner tube through the reinforcement such as the uniform spacing between the turns of the flat wire coil as previously described. By way of example, delivery system 73 and, in particular, delivery catheter 83 can be far greater in length than previously described introducer sheaths 10 and 40. In this embodiment of the delivery catheter of the present invention, the length of delivery catheter or sheath 83 can extend up to and through 125 centimeters hub to tip, which is known as the working length of the catheter. Also by way of example, delivery catheter 83 has a 6 French outside diameter of, for example, 0.87 inches with an inside diameter of approximately 0.57 inches with a wall thickness of 0.125 inches proximal distal portion 87 of the catheter. Accordingly, smaller diameter 101 can be considered to be the 0.57 inch diameter for purposes of this example. Likewise, the delivery catheter has a 6 French outside diameter of approximately 0.82 inches through distal portion 87 of the catheter with larger inside diameter 100 through distal portion 87 being approximately 0.76 inches with everted distal portion 87 having a wall thickness of approximately 0.03 inches. The length of the distal portion is typically 3 centimeters longer than that of the stent to be contained within the distal portion of the catheter and the annular recess of the pusher. Typically, for a ZILVER stent of approximately 8 centimeters in length, the length of the distal portion would be 11 centimeters. Reinforcement 86 such as a stainless steel flat wire coil with the turns thereof having a thickness of approximately 0.03 inches and a width of 0.012 inches as previously described. Uniform spacing between the turns of the flat wire coil are preferably 0.02 inches ranging from 0.01 to 0.06 inches approximately.

FIG. 9 also depicts pusher 75 with an inner tube of, for example, a braided polyimide material with passageway or lumen 77 extending therethrough. The diameter of this passageway has a diameter of approximately 0.40 inches to accommodate standard guide wires. The outside diameter is approximately 0.505 inches with a wall thickness of approximately 0.0525 inches. The length of this proximal, pusher inner tube extends almost the entire length of the pusher of which a distal end tube of, or example, polyamide such as, for example, radiopaque nylon braided material is expanded to be inserted over the distal end of inner pusher tube 76. The expanded outer diameter of 0.57 inches of the distal end pusher tube closely approximates the larger inner diameter of the distal portion of the delivery catheter having, for example, a 0.76 inch diameter. This 4.1 French distal end pusher tube has an inside diameter of approximately 0.39 inches. The distal pusher tube is glued to the inner pusher tube using, for example, Loctite No. 4011 glue. A radiopaque marker sleeve 81, of, for example, platinum, is positioned distal of the expanded proximal end of the distal end pusher tube to provide a shoulder at proximal end 96 of annular recess 92 of the pusher. Should the radiopaque marker not be desired, the expanded proximal end of the distal end pusher tube acts as shoulder 97 of which to engage the proximal end of the contained stent.

Pusher 75 also includes a radiopaque, distal tip biocompatible material having a maximum outside diameter of 0.750 inches equal to that of the distal portion of the delivery catheter. Distal tip 79 has a tapered distal end 80 and a smaller diameter proximal end 82 for receiving the open distal end of the delivery catheter. Distal end pusher tube 78 extends into the distal tip and is glued therein. Passageway or lumen 77 extends longitudinally throughout the entire length of the pusher to again accommodate receiving a standard guide wire. As a result, the proximal end of the distal tip and the enlarged proximal end of distal end 78 provides annular recess 92 of which to compress, for example, an implantable medical device such as a self-expanding stent. In addition, the expanded proximal end of the distal end tube is glued onto the distal end of inner pusher tube 76, using, for example, a medical grade adhesive.

Figure 12:
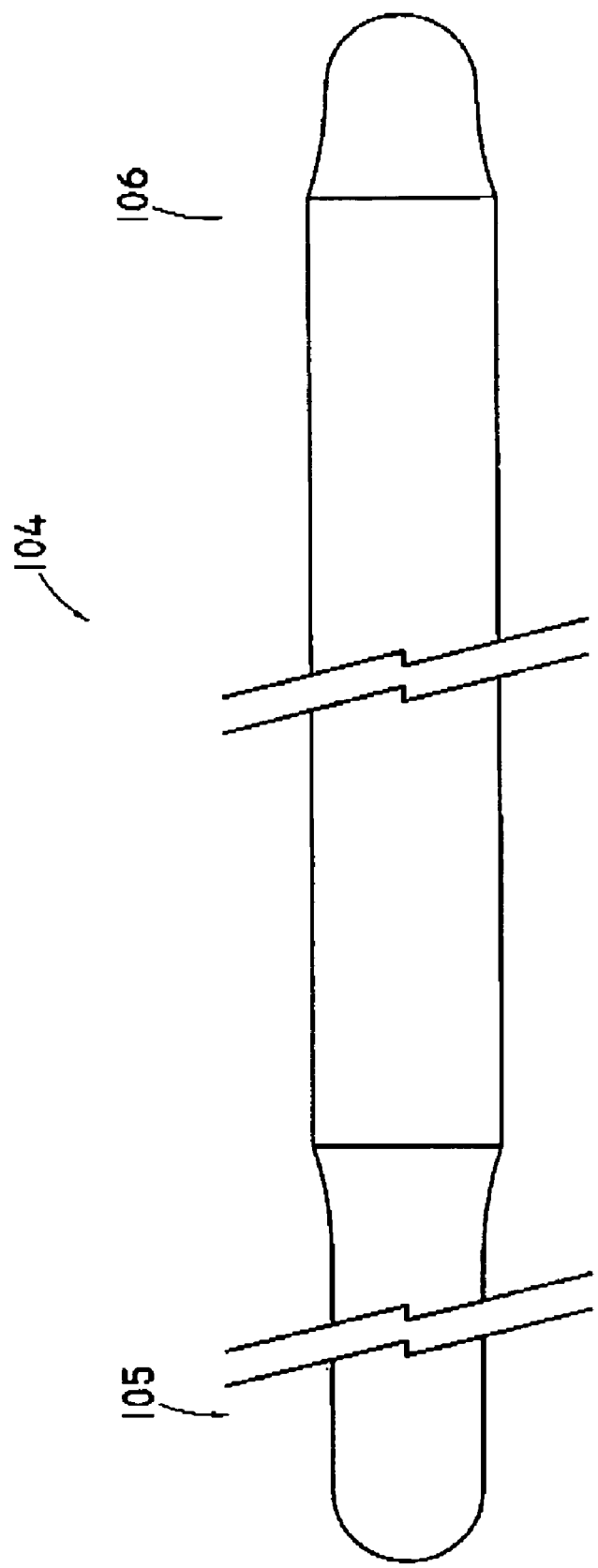
FIG. 12 depicts a mandril used to expand the inner diameter of the distal portion of the delivery catheter inner tube of FIG. 9.

FIG. 12 depicts mandril 104 that is used to expand or enlarge diameter 100 of distal portion 87 of delivery catheter inner tube 84. The mandril includes a proximal portion 105 having a diameter of approximately 0.58 inches and a distal portion 106 having an enlarged diameter of, for example, 0.82 inches.

Figure 13:
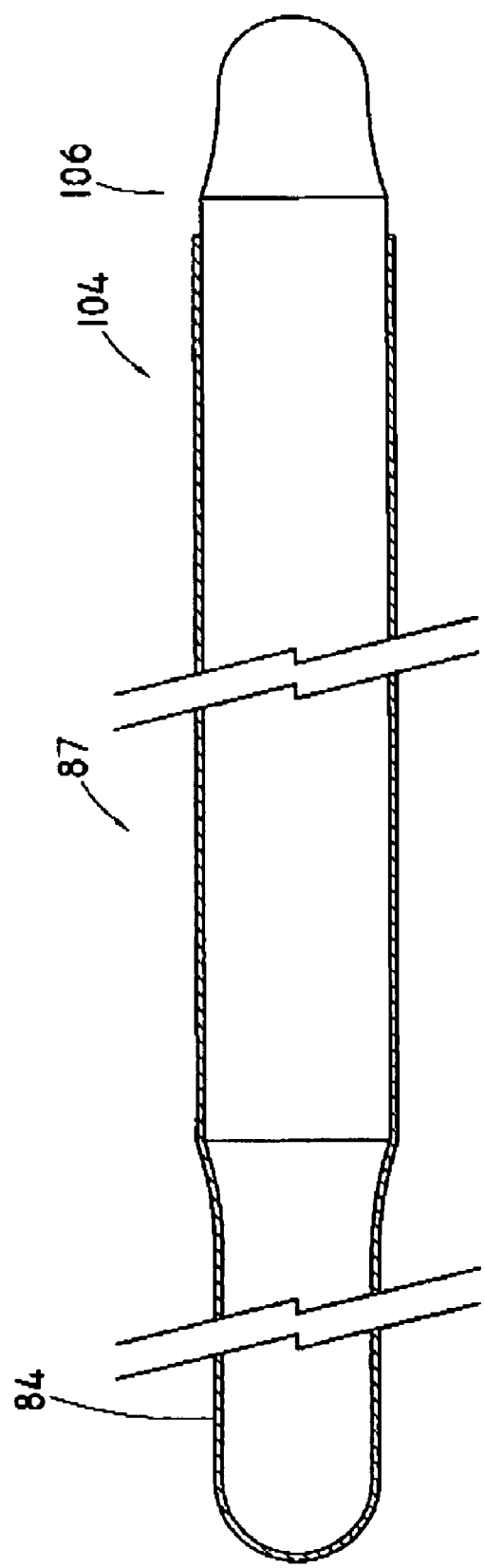
FIG. 13 depicts the mandril of FIG. 12 with delivery catheter inner tube positioned thereover.

FIG. 13 depicts mandril 104 with delivery catheter tube 84 positioned thereover. In this example, the inner delivery catheter tube has a wall thickness of approximately 0.02 inches proximal distal portion 87 and a wall thickness of approximately 0.01 inches through distal portion 87 due to expansion and thinning of the material when positioned over distal portion 106 of the mandril.

Figure 14:
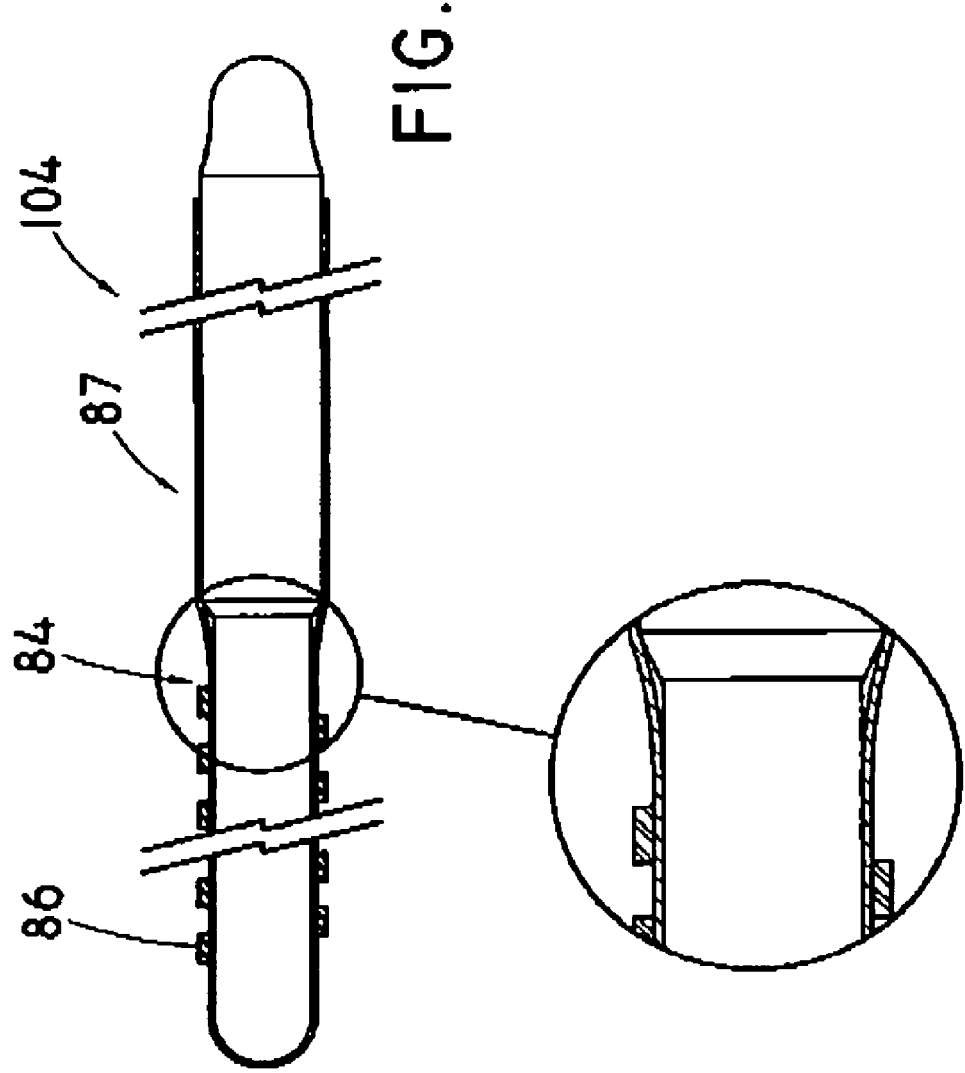
FIG. 14 depicts the placement of a reinforcement around the delivery catheter inner tube proximal the distal portion thereof.

FIG. 14 depicts reinforcement 86 or preferably flat wire coil being positioned along and around inner tube 84 proximal distal portion 87.

Figure 15:
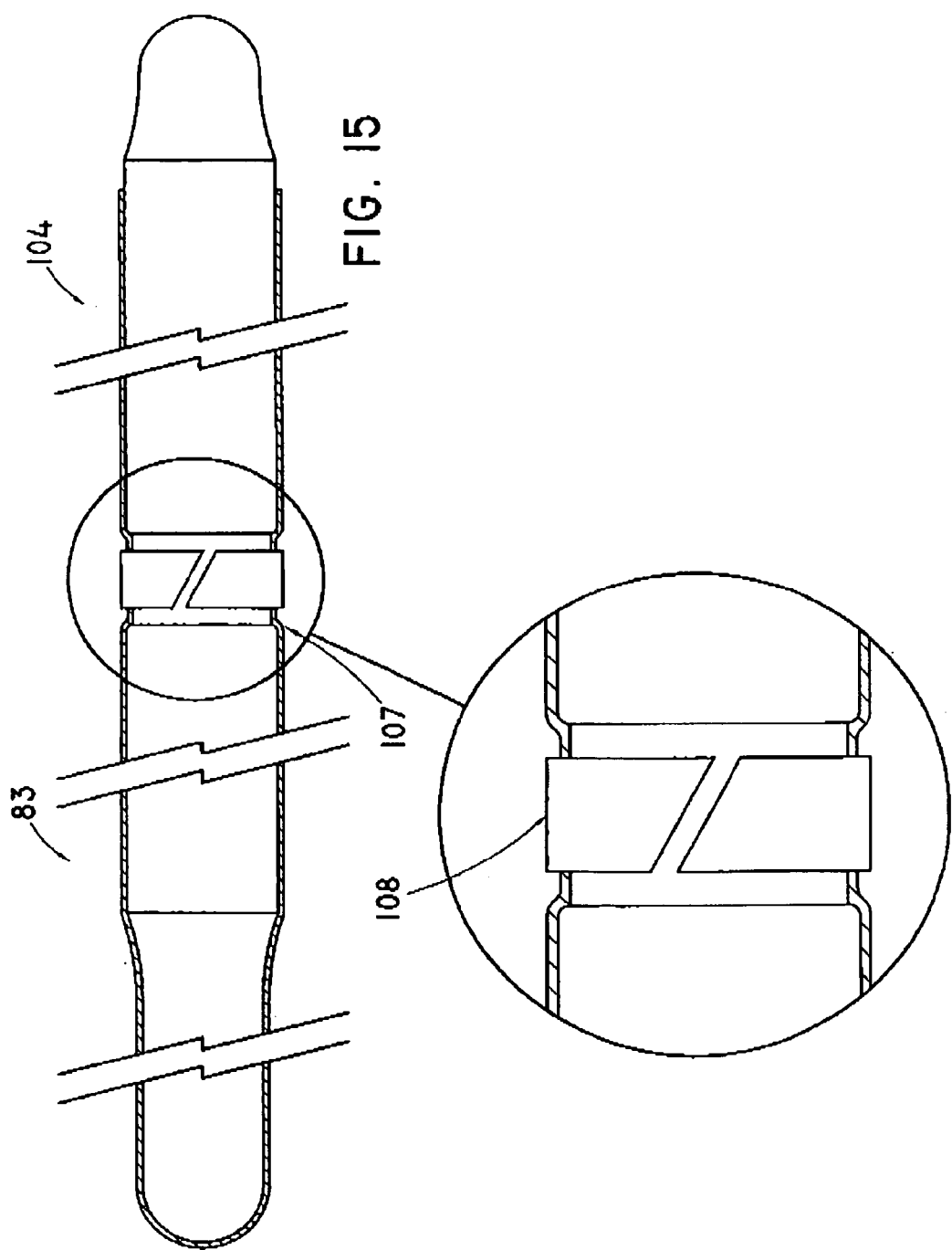
FIG. 15 depicts an alternative embodiment of the delivery catheter of the present invention positioned on the mandril of FIG. 13 with an annular recess therein.

FIG. 15 depicts an alternative embodiment of delivery catheter 83 of the present invention positioned on mandril 104 with an annular recess 107 to accommodate positioning a split radiopaque marker sleeve 108 to be positioned at the distal end of the distal portion of the delivery catheter.

Figure 16:
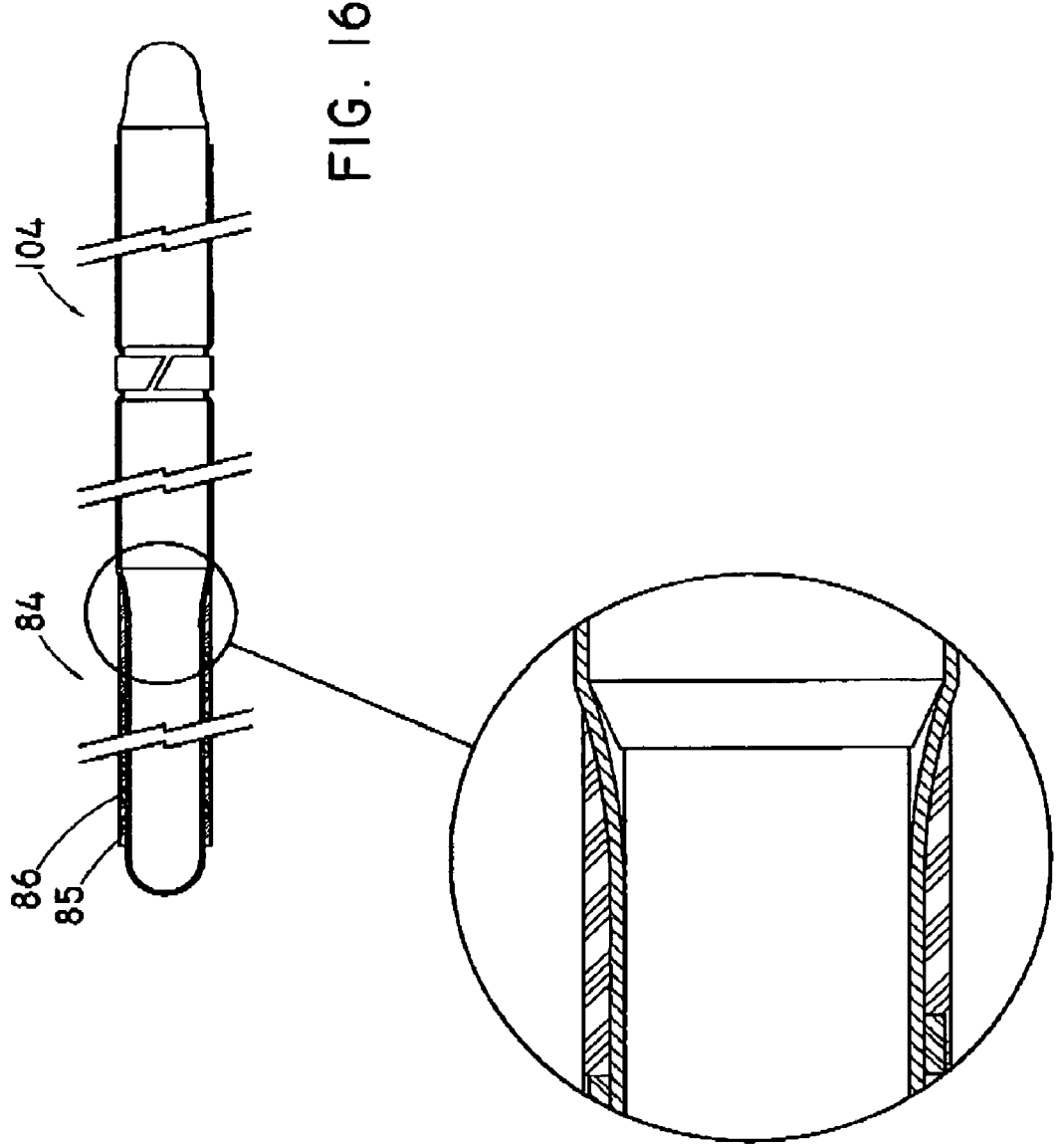
FIG. 16 depicts the inner delivery catheter tube on the mandril of FIG. 15 with the outer tube and reinforcement of positioned proximal the distal portion of the inner tube.

FIG. 16 depicts inner delivery catheter tube 84 on mandril 104 with outer delivery catheter tube 85 positioned around and proximal distal portion 87 and through reinforcement 86 such as flat wire coil turns as previously discussed.

Figure 17:
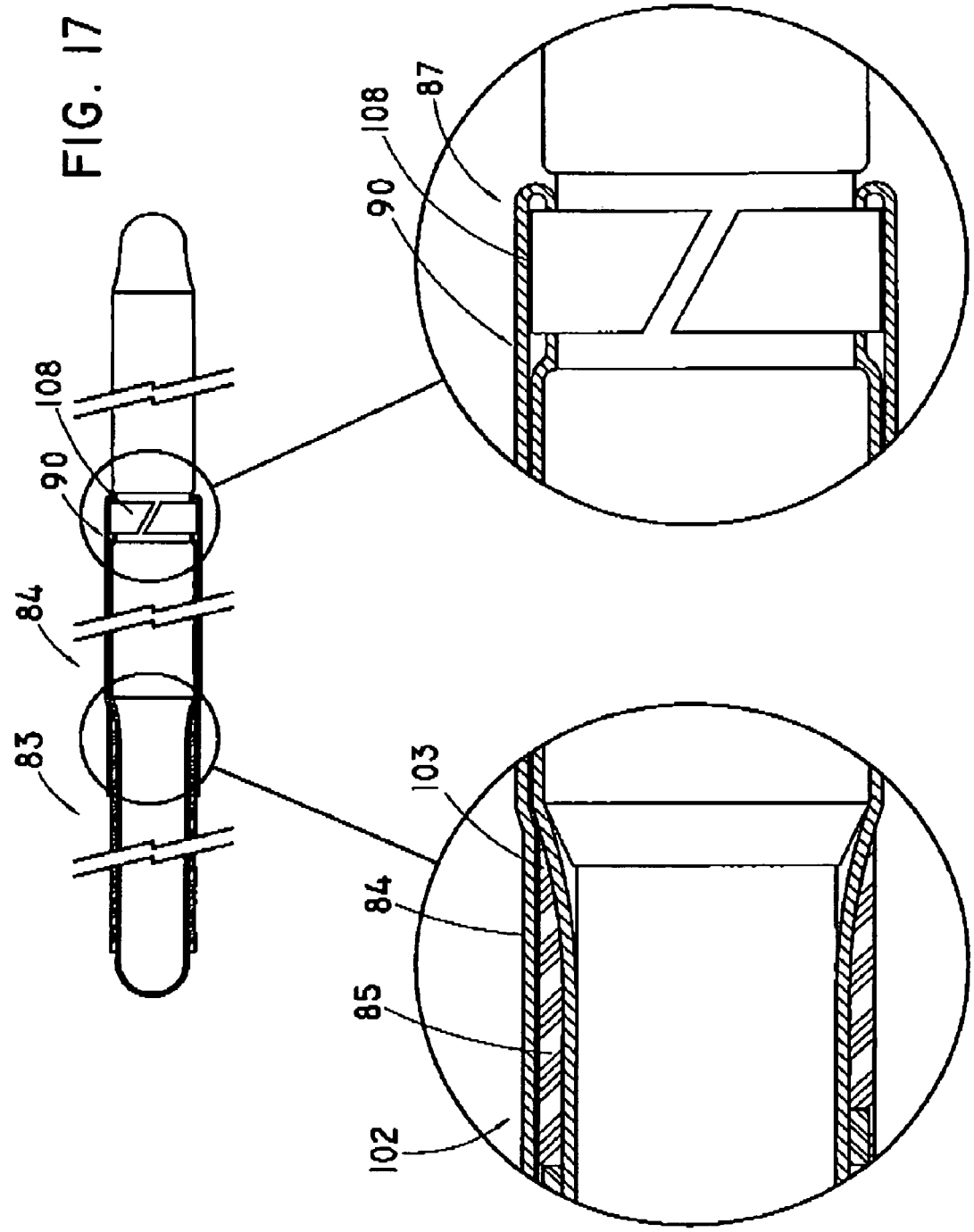
FIG. 17 depicts the delivery catheter of FIG. 16 with the inner tube being folded back or everted over itself.

FIG. 17 depicts delivery catheter 83 of FIG. 16 with inner tube 84 being folded back or everted over itself and connected to outer tube 85. The distal end 102 of the inner tube is connected to the distal end 103 of the outer tube with the aid of medical grade adhesive 90, as previously described. As a result of this fold back, marker sleeve 108 is now positioned at the distal end of distal portion 87 of the delivery catheter. Although shown with sleeve marker 108, the preferred embodiment of the delivery catheter does not include this marker sleeve and is simply not positioned on the mandril and inner tube during the manufacturing process.

Figure 18:
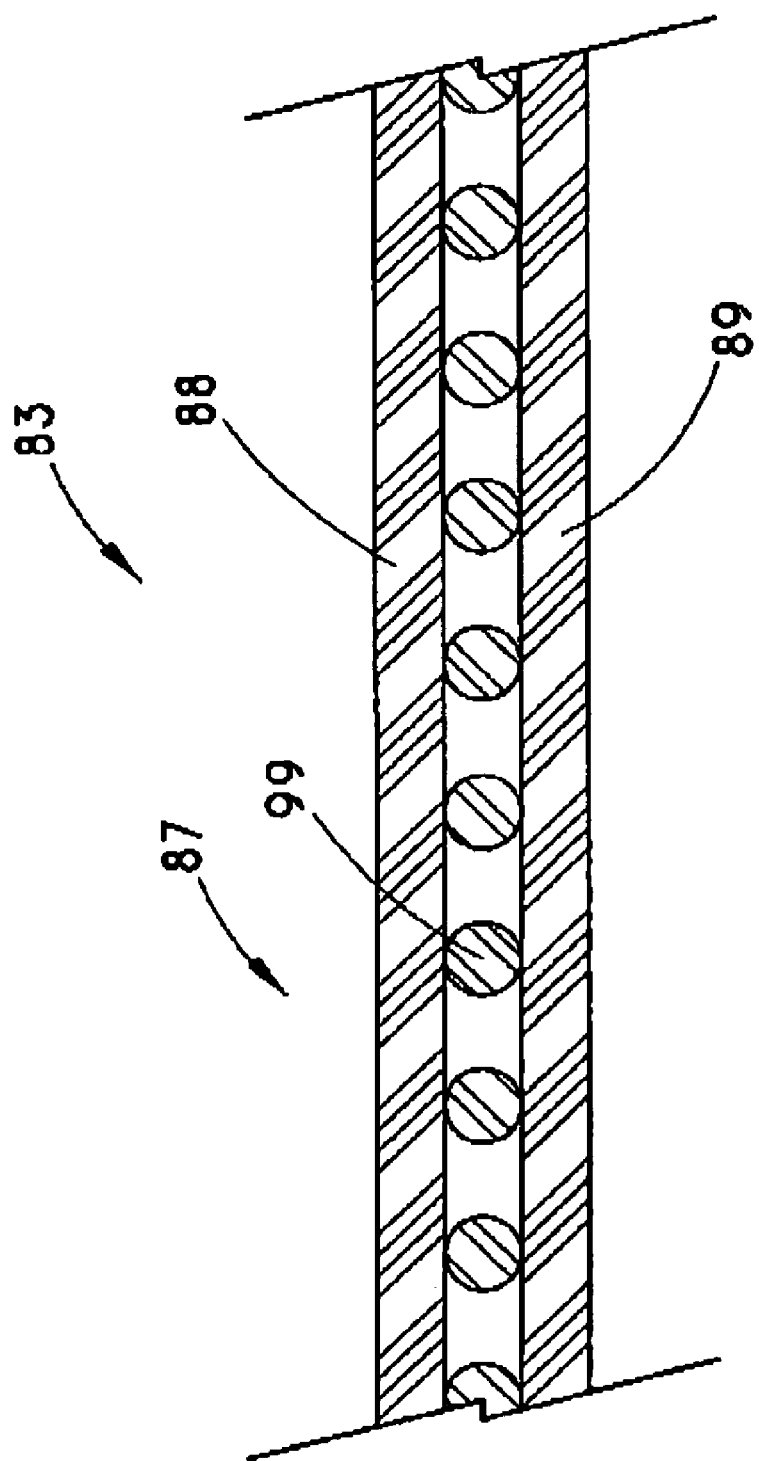
FIG. 18 depicts an enlarged and sectioned view of still another alternative embodiment of the distal portion of the delivery catheter of the present invention.

FIG. 18 depicts an enlarged and sectioned view of still another alternative embodiment of distal portion 87 of delivery catheter 83. In this construction of the distal portion of the catheter, two separate coaxial layers of material 88 and 89 sandwich reinforcement 99 therebetween. In particular, the first outer layer of the distal portion includes a 0.01 inch thickness of PTFE or a polyimide material. Likewise second or inner layer 89 of the distal portion has a like thickness of PTFE or polyimide material. Reinforcement 99 can be simply a coil of filament suture material, a winding of cylindrical wire uniformly spaced to form a coil or a flat wire coil with uniform spacing between the coil turns. The uniform spacing can be maintained by compression fitting the coil. The dimensions of the rectangular or flat wire coil are approximately 0.05 inches thick and 0.03 inches wide. Alternatively, inner layer 89 can be a PEBAX-72D material as previously described. Thus the overall thickness of the distal portion wall will not exceed 0.03 inches. This is to advantageously provide the largest diameter containment vessel for the implantable medical device. The reinforcement in the distal portion of the catheter prevents the implantable medical device from expanding into the material and enlarging or pushing the material outwards. This is particularly noticed with a self-expanding stent that embeds itself into the distal portion material over an extended period of time. The reinforcement 99 inhibits or prevents such expansion of the distal catheter portion. Such a coaxial and reinforced material is commercially available from MedSource Technologies, Trenton, Ga. It is to be understood that the above-described flexible, kink-resistant, delivery catheter or sheath is merely an illustrative embodiment of the principles of this invention and that other delivery catheters or sheaths may be devised by those skilled in the art without departing from the spirit and scope of this invention. It is contemplated that various other materials may be utilized for the inner, outer, and heat shrink tubes. It is also contemplated that delivery catheters or sheaths with an inside diameter ranging in size from 4.0 to 14.0 French are readily producible. In summary, the flexible, kink-resistant, delivery catheter or sheath provides a thin-wall delivery catheter or sheath that is extremely kink-resistant for long-term use applications. The flat wire coil construction of this delivery catheter or sheath is also extremely kink-resistant with small outside diameter dilators during introduction through an access site.

What is claimed is:

1. A delivery system comprising:
a delivery catheter comprising an inner tube having a passageway extending longitudinally therein, a distal portion of said inner tube being everted and comprising first and second coaxial layers, said first and second coaxial layers being joined by an adhesive along a length thereof, said inner tube passageway having a larger diameter in said distal portion having said joined coaxial layers than in a remainder of said passageway; and an outer tube bonded to said inner tube proximal said distal portion of said inner tube, a distal portion of said outer tube disposed between a proximal length of said first and second coaxial layers, and
a pusher disposed in said passageway of said inner tube, said pusher having an annular recess in a distal portion thereof received in said larger diameter passageway.

2. The delivery system of claim 1, wherein said pusher has a radiopaque marker disposed about a proximal end of said annular recess.

3. The delivery system of claim 1, wherein said pusher has a shoulder at a proximal end of said annular recess and engaging said distal portion of said inner tube about said passageway.

4. The delivery system of claim 1, wherein said pusher has a distal tip disposed distal said annular recess and has a tapered portion extending from said inner tube, said pusher further having a proximal portion capable of engaging said inner tube about said passageway.

5. The delivery system of claim 1, wherein a proximal end of said everted portion extends proximal said annular recess of said pusher.

6. The delivery system of claim 1, wherein said distal portion of said inner tube includes a reinforcement between said first and said second layers of said inner tube.

7. The delivery system of claim 6, wherein said reinforcement includes at least one of a coil of suture and wire sandwiched between said first and said second layers of said tube, and wherein said outer tube is bonded to said inner tube through said reinforcement.

8. A delivery catheter comprising:
an inner tube having an inner passageway extending longitudinally therein, a distal portion of said inner tube being everted, said everted portion comprising first and second coaxial layers, an outer surface of said first coaxial layer being adhesively joined to an inner surface of said second coaxial layer along a distal length of said everted portion, said inner passageway having a larger diameter along said distal length of said inner tube than in a remainder of said passageway; and
an outer tube proximal said distal portion of said inner tube, a distal portion of said outer tube disposed between said first and second coaxial layers along a proximal length of said everted portion, said outer tube having an inner surface, said inner surface bonded to an outer surface of said inner tube.

9. The delivery catheter of claim 1, wherein said first and second coaxial layers are adhered together along said larger diameter distal portion of said first tube.

10. The delivery catheter of claim 9, wherein said distal portion of said pusher having said annular recess is disposed interiorly of said larger diameter distal portion of said first tube.

11. The delivery catheter of claim 8 further comprising:
a reinforcement positioned at least partially along and proximal said distal portion of said inner tube; and
wherein said outer tube is positioned around said reinforcement.

12. The delivery catheter of claim 8, wherein said inner tube comprises a lubricious material.

13. The delivery catheter of claim 11, wherein said reinforcement comprises a coil having a plurality of coil turns, and wherein said outer tube is bonded to the inner tube through the coil turns.

14. The delivery catheter of claim 8, wherein said adhesive comprises a medical grade adhesive.

15. The delivery catheter of claim 14, wherein said medical grade adhesive comprises an ultra-violet light cured glue.

16. The delivery catheter of claim 14, wherein said medical grade adhesive comprises a hot melt glue.

* * * * *